ns010172532B1

United States Patent
Ni et al.

(10) Patent No.: US 10,172,532 B1
(45) Date of Patent: Jan. 8, 2019

(54) FEATURE TRANSFORMATION OF NEURAL ACTIVITY WITH SPARSE AND LOW-RANK (SLR) DECOMPOSITION

(71) Applicant: HRL Laboratories, LLC, Malibu, CA (US)

(72) Inventors: Kang-Yu Ni, Calabasas, CA (US); James Benvenuto, Beverly Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 995 days.

(21) Appl. No.: 14/626,915

(22) Filed: Feb. 19, 2015

(51) Int. Cl.
*A61B 5/00* (2006.01)
*A61B 5/04* (2006.01)
*A61B 5/0484* (2006.01)
*A61B 5/055* (2006.01)

(52) U.S. Cl.
CPC ........ *A61B 5/04012* (2013.01); *A61B 5/0075* (2013.01); *A61B 5/04009* (2013.01); *A61B 5/0484* (2013.01); *A61B 5/055* (2013.01); *A61B 5/7271* (2013.01)

(58) Field of Classification Search
CPC .......................... A61B 5/04012; A61B 5/0075
See application file for complete search history.

(56) References Cited

PUBLICATIONS

Basri, Ronen, and David W. Jacobs, "Lambertian reflectance and linear subspaces," Pattern Analysis and Machine Intelligence, IEEE Transactions on 25.2, pp. 218-233, 2003.

Kohavi, Ron, "A study of cross-validation and bootstrap for accuracy estimation and model selection," IJCAI, vol. 14. No. 2, 1995.

Cortes, Corinna, and Vladimir Vapnik, "Support-vector networks," Machine learning 20.3, pp. 273-297, 1995.

E. Candes, X. Li, Y. Ma, and J. Wright, "Robust Principal Component Analysis?" IEEE PAMI 2011, pp. 201-204.

S. J. Gilbert. "Decoding the content of delayed intentions," J Neurosci, 31, pp. 2888-2894, 2011.

T. M. Mitchell, S. V. Shinkareva, A. Carlson, K.-M. Chang, V. L. Malave, R. A. Mason and M. A. Just, "Predicting human brain activity associated with the meanings of nouns," Science, 320(5880), pp. 1191-1195, 2008.

J. Mourao-Miranda, A. L. Bokde, C. Born, H. Hampel, and M. Stetter, "Classifying brain states and determining the discriminating activation patterns: support vector machine on functional MRI data," Neuroimage 28, pp. 980-995 (2005).

(Continued)

*Primary Examiner* — Nadia A Mahmood
(74) *Attorney, Agent, or Firm* — Tope-McKay & Associates (57) ABSTRACT

Described is system for feature transformation of neural activity using sparse and low-rank (SLR) decomposition. A set of neural activity signals associated with different stimuli are obtained, and a neural feature is extracted or each stimuli from the set of neural activity signals using SLR decomposition. The neural feature is then used to generate a classification of the stimuli. The neural activity signals may include functional magnetic resonance imaging (fMRI) signals, fMRI blood-oxygen-level dependent (BOLD) signals, electroencephalography (EEG) signals, functional near-infrared spectroscopy (fNIRS) signals, or magnetoencephalography (MEG) signals. The system according to the principles of the present invention will he an important component of any neural activity based classification system.

21 Claims, 5 Drawing Sheets

(56) References Cited

PUBLICATIONS

T. Zhou and D. Tao. "GoDec: Randomized low-rank & sparse matrix decomposition in noisy case," ICML 2011.

Huth, A. G., Nishimoto, S., Vu, A. T., & Gallant, J. K. (2012). A continuous semantic space describes the representation of thousands of object and action categories across the human brain. Neuron, 76(6), pp. 1210-1224.

Mitchell, T. M., Shinkareva, S. V., Carlson, A., Chang, K.-M., Malave, V. L., Mason, R. A., & Just, M. A. (2008). Predicting human brain activity associated with the meanings of nouns. Science, 320(5880), pp. 1191-1195.

FIG. 5 ically based. This 30
FEATURE TRANSFORMATION OF NEURAL ACTIVITY WITH SPARSE AND LOW-RANK (SLR) DECOMPOSITION

GOVERNMENT LICENSE RIGHTS

This invention was made with government support under U.S. Government Contract Number Contract # FA8650-13-C-7356. The government has certain rights in the invention

FIELD OF INVENTION

The present invention relates to a system for feature transformation of neural activity and, more particularly, to a system for feature transformation of neural activity using sparse and low-rank (SLR) decomposition.

BACKGROUND OF THE INVENTION

Feature selection and feature transformation are very important components in any neural activity classification pipeline. Generally, neural activity data is very noisy. One source of noise comes from the technology used to extract the neural signals. This can be signal drift caused by, for example, the device for measuring neural activity "warming-up" over time, inhomogeneities of a magnetic field used to measure the signals, variance in conductance of any electrodes receiving signals, and general noise introduced by electronic circuits.

Another source of noise is physiologically based. This includes, for example, fluctuations caused by movement, variation in heart rate, changes in skin resistance, and blinking of the subject. Finally, the most complex form of noise is random off-task mental activity by the subject. Given this complexity and the high dimensionality of neural activity signals, classification of brain states via these signals is difficult and error prone.

Numerous methods have been developed to deal with this difficulty. Given the large number of data dimensions available, one class of techniques tries to determine which dimensions are more informative and throw the others out, thereby reducing the dimensionality of the problem. Selecting "stable" voxels (a single data point on a regularly spaced, three-dimensional grid), as described in Literature Reference No. 3 of the List of Incorporated Cited Literature References, is one such technique. Another technique is using some discriminant measure to rank voxels.

In addition to reducing the number of dimensions, transformations over the representation space has also been performed. A common method for this is using Singular Value Decomposition (SVD) to transform the data (see Literature Reference No. 4 for a description of SVD). The SVD method prioritizes data according to variance, but may not correlate with discriminability. Another method is linear regression to extract the beta coefficients as an alternative representation of the data, as described in Literature Reference No. 2.

While the prior methods described above are able to reduce the dimensionality of neural activity data, they are not designed to distinguish neural activity patterns. Because of the high dimensionality of the data (due to noise and over abundant measurements) and the actual information, content is embedded within a much lower dimensional manifold. Thus, a continuing need exists for a system for accessing the content via sparse and low-rank (SLR) decomposition to find the representation of the signal content amongst the high-dimensional data signal.

SUMMARY OF THE INVENTION

The present invention relates to a system for feature transformation of neural activity and, more particularly, to a system for feature transformation of neural activity using sparse and low-rank (SLR) decomposition. The system comprises one or more processors and a memory having instructions such that when the instructions are executed, the one or more processors perform multiple operations. The system obtains a set of neural activity signals associated with different stimuli, and extracts a neural feature for each stimuli from the set of neural activity signals using sparse and low-rank (SLR) decomposition. The neural feature is used to generate a classification of the stimuli.

In another aspect, the neural feature for each stimuli is stored as a set of voxels, each voxel having a vector value.

In another aspect, the neural activity signals are functional magnetic resonance imaging (fMRI) neural activity signals, and the system selects a set of stable voxel values from a collection of fMRI brain volumes associated with the different stimuli. From the set of stable voxel values, a set of fMRI brain volumes associated with the set of stable voxel values is organized into a matrix X. The matrix X is then decomposed into a set of matrices: a low-rank part L matrix, a sparse part S matrix, and a Gaussian part G matrix.

In another aspect, the sparse part S matrix represents a neural activation feature, the low-rank L matrix represents a neural resting state feature, and the Gaussian part G matrix represents noise.

In another aspect, the neural activation feature is modeled as a foreground in the set of neural activity signals, and the neural resting state feature is modeled as a stationary background in the set of neural activity signals.

In another aspect, the set of stable voxel values comprises exemplar-activated voxels representing a current focus of attention, and the system extracts exemplar-activated voxels from the set of stable voxels.

In another aspect, the neural activity signals are selected from a group consisting of functional magnetic resonance imaging (fMRI) neural activity signals, fMRI blood-oxygen-level dependent (BOLD) neural activity signals, electroencephalography (EEG) neural activity signals, functional near-infrared spectroscopy (fNIRS) neural activity signals, and magnetoencephalography (MEG) neural activity signals.

In another aspect, the present invention also comprises a method for causing a processor to perform the operations described herein.

Finally, in yet another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a system for feature transformation of neural activity and, more particularly, to a system for feature transformation of neural activity using sparse and low-rank (SLR) decomposition. The following description is presented to enable one of ordinary skill in the art to make and use the invention and to incorporate it in the context of particular applications. Various modifications, as well as a variety of uses in different applications will readily apparent to those skilled in the art, and the general principles defined herein may be applied, to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation.

Before describing the invention in detail, first a list of cited literature references used in the description is provided. Next, a description of various principal aspects of the present invention is provided. Finally, specific details of the present invention are provided to give an understanding of the specific aspects.

(1) List of Incorporated Cited Literature References

The following references are cited throughout this application. For clarity and convenience, the references are listed herein as a central resource for the reader. The following references are hereby incorporated by reference as though fully included herein. The references are cited in the application by referring to the corresponding literature reference number, as follows:

1. E. Candes, X. Li, Y. Ma, and J. Wright, "Robust Principal Component Analysis?", IEEE PAMI 2011.
2. S. J. Gilbert. "Decoding the content of delayed intentions". J. Neurosci, 31: 2888-2894, 2011.
3. T. M. Mitchell, S. V. Shinkareva, A. Carlson, K.-M. Chang, V. L. Malave, R. A. Mason and M. A. Just, "Predicting human brain activity associated with the meanings of nouns", Science, 320(5880), 2008.
4. J. Mourao-Miranda, A. L. Bokde, C. Born, H. Hampel, and M. Stetter, "Classifying brain states and determining the discriminating activation patterns: support vector machine on functional MRI data", Neuroimage 28, 980-995, 2005.
5. T. Zhou and D. Tao. "GoDec: Randomized low-rank & sparse matrix decomposidon noisy case." ICML, 2011.
6. Basri, Ronen, and David W. Jacobs. "Lambertian reflectance and linear subspaces." Pattern Analysis and Machine Intelligence, IEEE Transactions on 25.2, 218-233, 2003.
7. Kohavi, Ron. "A study of cross-validation and bootstrap for accuracy estimation and model selection." IJCAI. Vol. 14. No. 2, 1995.
8. Cortes, Corinna, and Vladimir Vapnik, "Support-vector networks." Machine learning 20.3, 273-297, 1995.

(2) Principal Aspects

The present invention has three "principal" aspects. The first is a system for feature transformation of neural activity. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will he described in more detail below.

Figure 1:
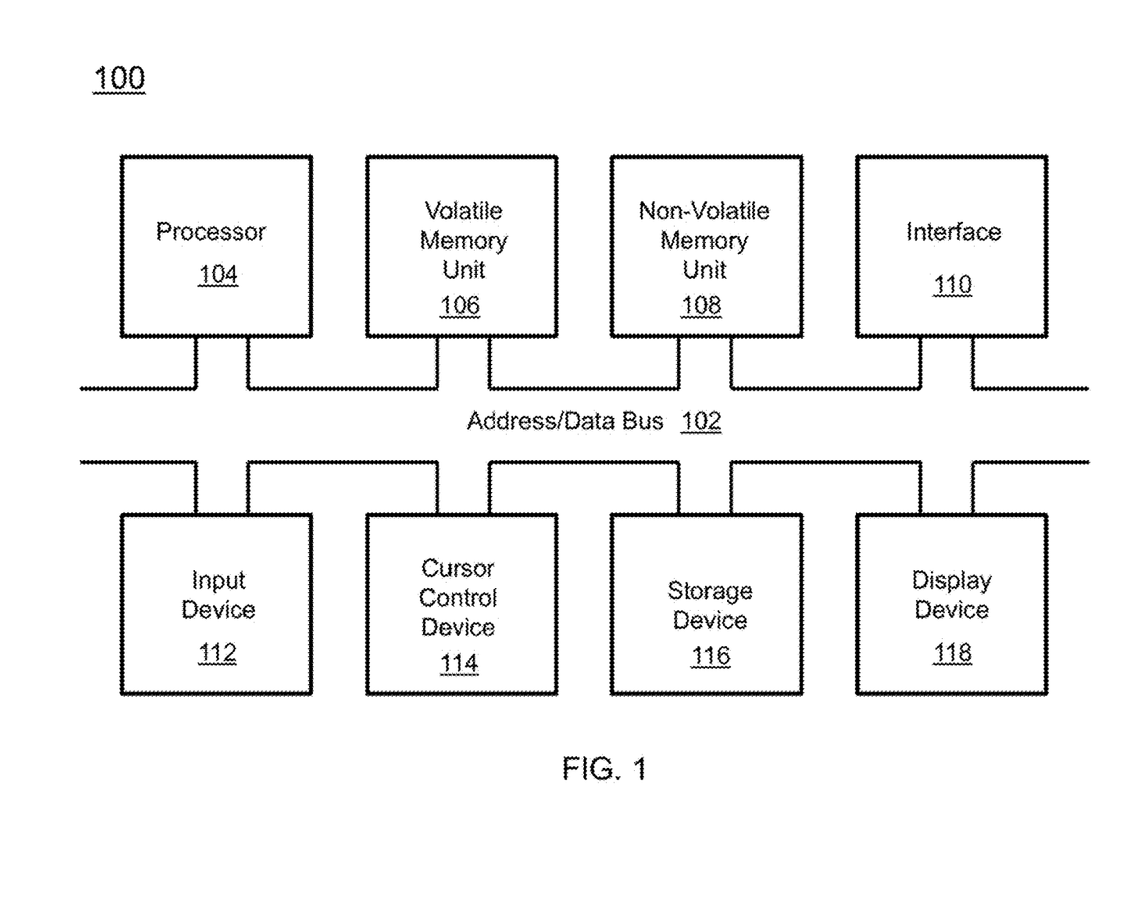
FIG. 1 is a block diagram depicting the components of a system for feature transformation of neural activity according to the principles of the present invention.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, or a field programmable gate array.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store inthrmation and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing, notwithstanding, in an aspect, the cursor control device 114 is directed and/or activated via input from the input device 112, such as in response to the use of special keys and key sequence commands associated with the input device 112, in an alternative aspect, the cursor control device 114 is configured to he directed or guided by voice commands.

In an aspect, the computer system 100 further may include one or more optional computer usable data storage devices, such as a storage device 116, coupled with the address/data bus 102, The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect, However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to an single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
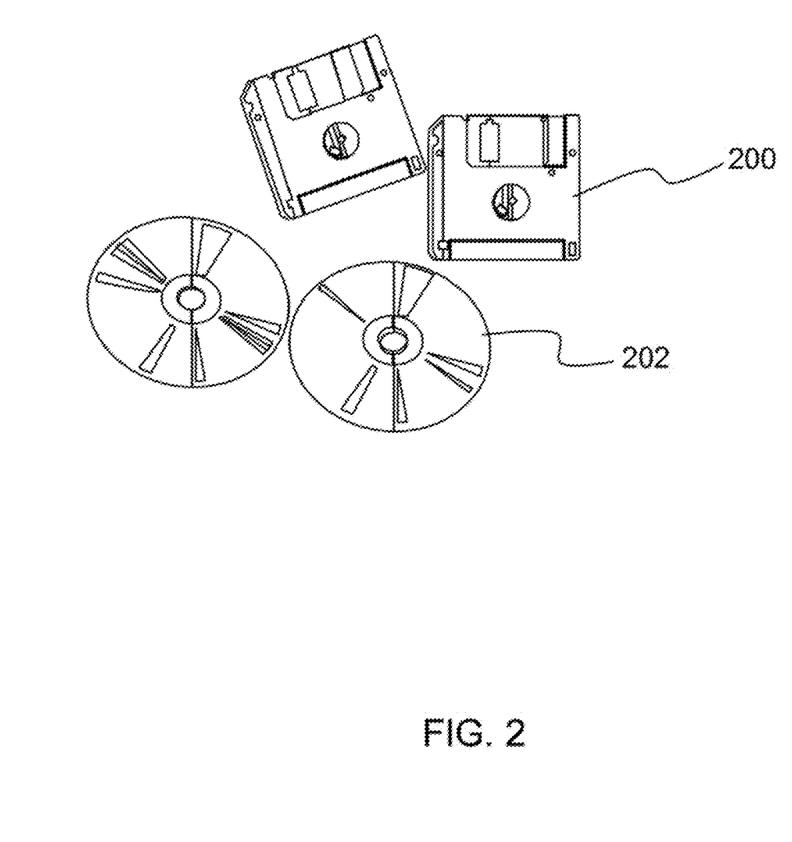
FIG. 2 is an illustration or a computer program product according to the principles of the present invention.

An illustrative diagram of a computer program product (i.e., storage device) embodying an aspect of the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code and "hard-coded" electronics computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of the Invention

Described is a feature transformation system that extends the sparse and low-rank (SLR) decomposition method (see Literature Reference No. 1 for a description of the SLR decomposition method) to neural activity signals associated with different stimuli, including, but not limited to, visual concept stimuli. A non-limiting example of a visual concept stimuli is a picture of any object, such as a bear, cat, cow, arm, foot, apartment, and house. The system according to the principles of the present invention is based on novel use of SLR matrix decomposition to extract neural features for classification of neural activity signals. This technique will be an important component of any neural activity based classification system.

The neural domains to be classified can come from any number of signals, non-limiting examples of which include signals from functional magnetic resonance imaging (fMRI), fMRI blood-oxygen-level dependent (BOLD), electroencephalography (EEG), functional near-infrared spectroscopy (fNIRS), and magnetoencephalography (MEG). The data from these initially noisy high-dimensional complex neural domains often contain a foreground part and a background part in addition to the noise. The background part can represent resting state activity, or normal ongoing maintenance activity, while the foreground activity might represent a current focus of attention or activity. The present invention can separate the foreground part from the background part and enable more accurate classification of the signals, especially when the signal of interest pertains to either foreground or background activity.

The system according to the principles of the present invention increases stimuli classification accuracy from neural activity patterns. While the embodiment of the invention described herein is based on decoding fMRI brain images, the present invention can be applied to any neural activity signal, such as those described above. The fMRI brain images are extremely noisy because of the mechanics of signal extraction, physiological noise, and the existence of non-task related mental activity. This noise cannot be modeled by a simple model, such as additive Gaussian noise. Therefore, to be able to classify different exemplars (e.g., pictures of objects, such as a cat, cow, hand, apartment, or barn) with high accuracy, the voxel values of the fMRI brain volume cannot be directly used. The present invention, therefore, applies the (SLR) decomposition method to transform the voxel values in order to increase classification accuracy. Specifically, the SLR decomposition is used to extract exemplar activation (which is sparse spatially) from a resting state. Exemplar activation may refer to neural activity signals from one or more persons that were acquired while the one or more persons were presented with stimuli (e.g., exemplars). The resting state may refer to neural activity signals that were acquired from the one or more persons while the one or more persons were presented with a baseline stimuli such as a blank screen or flashcard, or simply being at the same location where stimuli is presented before, after, and/or between presentation of stimuli to the one or more persons.

(3.1) Sparse and Low Rank Decomposition

Sparse and low-rank (SLR) decomposition is a set of provably optimal and efficient mathematical techniques for identifying and decomposing low-variation structure of a scene from high-dimensional raw data (see Literature Reference No. 1). Suppose one has a stationary camera that is viewing a scene for the task of intruder/foreground detection. If many raw image frames are obtained over the course of a day, one can stack each frame as a column vector of the data matrix D, which can be decomposed to X=L+S, where L is the low-rank matrix that represents the background, and S is the sparse matrix that represents the sparse foreground and deviations from the convex Lambertian model (e.g., shadows and reflection). The convex Lambertian model is described in Literature Reference No. 6. The low-rank matrix L is extremely low-rank relative to the image size and the size of the columns in X. It is shown in Literature Reference No. 1 that the low-rank and sparse components of the data matrix D can be exactly decomposed by Principal Component Pursuit (PCP) according to the following:

$$\min_{A,E} \|L\|_* + \lambda \|S\|_1, \text{ such that } X = L + S,$$

where $\|L\|_*$ is the sum of the singular values of L, and $\|S\|_1$ is the absolute sum of entries of S. The minimizer L provides a background template for a stationary camera.

(3.2) Feature Transformation with SLR

The system according to the principles of the present invention uses the SLR decomposition to transform neural features from neural activity. The resting state is modeled as the "stationary background" and exemplar activations as "intruders". The resting state fMRI is a method of functional brain imaging that can be used to evaluate regional interactions that occur when a subject (i.e., person) is not performing an explicit task, or when no stimuli is presented to the subject. An exemplar activation can be a visual concept stimulus, a non-limiting example of which is a picture of an object shown to the subject.

Figure 3:
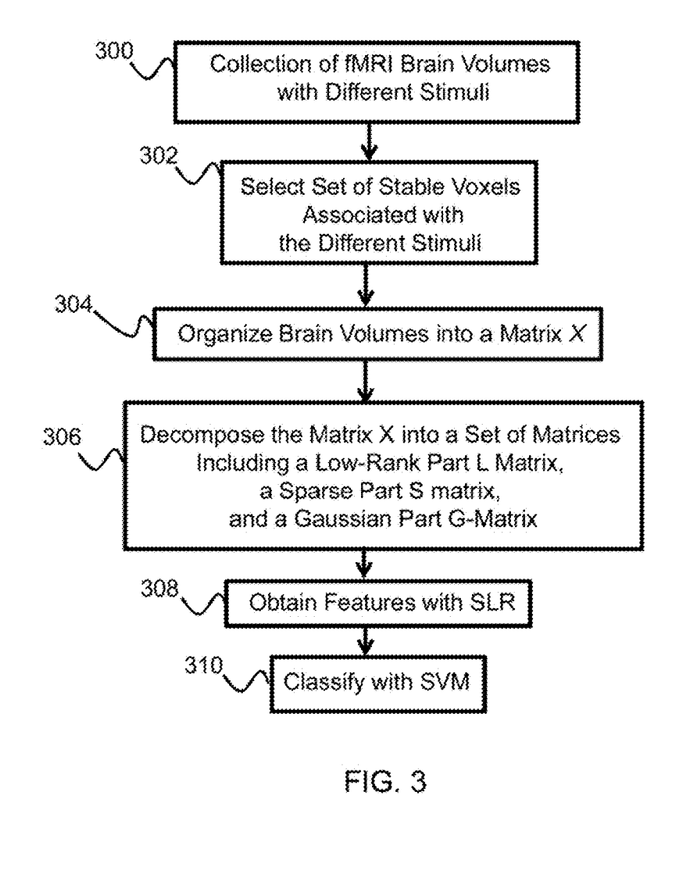
FIG. 3 is a flow diagram depicting feature transformation of neural activity according to the principles of the present invention.

FIG. 3 is a flow diagram depicting a non-limiting example of operation of the present invention, aspects of which will be described in detail below. Given a collection of input fMRI brain volumes with different stimuli (element 300), stable voxels are selected (i.e., select stable voxels, element 302). From the selected stable voxels, brain volumes are then organized into a matrix X (element 304), in which each column is a brain volume with the stable voxels. This matrix X is then decomposed into three matrices (element 306) followed by obtaining of features with SLR (element 308). Classification is performed using a linear support vector machine (SVM) (i.e., classify with SVM, element 310).

Figure 4:
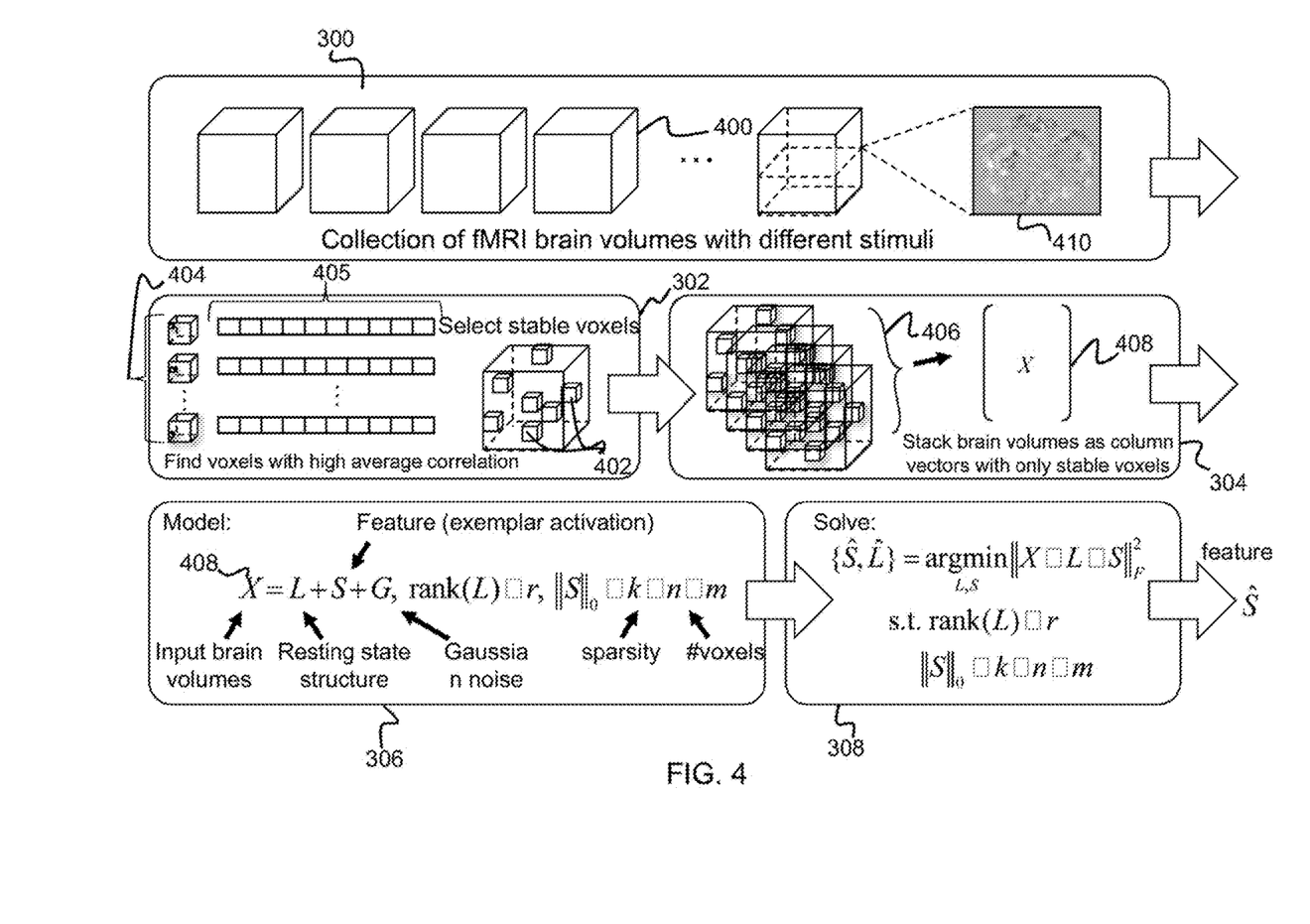
FIG. 4 is an illustration of feature transformation of neural activity according to the principles of the present invention.

FIG. 4 illustrates feature transformation of neural activity in further detail than FIG. 3. Given a collection 405 of input fMRI brain volumes 400 with different stimuli (element 300), a set of stable voxels 402 that are highly correlated across the brain volumes 400 are first selected (i.e., select stable voxels, element 302) from a plurality of voxels 404 (e.g., multiple voxels within each brain volume), since a large portion of the voxels 404 values are highly corrupted by noise. An image 410 represents a 2D (two-dimensional) cross-section of one of the fMRI brain volumes 400.

The set of stable voxels 402 are selected according to the most stable pattern of response to different stimuli across training runs. Pairwise correlations were determined between the patterns of responses (sorted by stimulus) for each pair of training runs for each voxel 404. Stability was defined, as the mean correlation across runs. Voxels 404 were sorted according to decreasing stability, and the first 2000 voxels 404 were selected as input to the classifier, as described below. From the set of selected stable voxels 402, a set of brain volumes 406 are then organized (or stacked) into a matrix X 408 (element 304), in which each column is a brain volume 400 with the set of stable voxels 402. This matrix X 408 is then decomposed into three matrices (element 306): a low-rank part L that represents the common resting state structure, a sparse part S that represents different exemplar activation, and a Gaussian noise part G:

$$X = L + S + G, \text{ rank}(L) \leq r, \|S\|_0 \leq k \times n \times m,$$

where r is a small integer compared to n (e.g., 1, 2, ..., 10), $\|\cdot\|_0$ is the $l_0$-norm that counts the number of non-zero entries, k is the sparsity percentage, n is the number of stable voxels in each brain volume, and m is the number of brain volumes. This formulation can be solved by the following optimization problem described in Literature Reference No. 5:

$$\{\hat{L}, \hat{S}\} = \underset{L,S}{\operatorname{argmin}} \|X - L - S\|_F^2 \text{ s.t. rank}(L) \leq r, \|S\|_0 \leq k \times n \times m,$$

where $\|\cdot\|_F$ is the Frobenius norm. The Frobenius norm is a matrix norm defined as $\|A\|_F \triangleq \sqrt{\Sigma_i \Sigma_j |a_{ij}|^2}$, where are the $ij^{th}$ entry of A.

The optimization problem is solved by alternating solving the following subproblems until convergence:

$$\begin{cases} L_t = \underset{L}{\operatorname{argmin}} \|X - L - S_{t-1}\|_F^2 & \text{subject to } \operatorname{rank}(L) \le r, \\ S_t = \underset{S}{\operatorname{argmin}} \|X - L_t - S\|_F^2, & \text{subject to } \|S\|_0 \le k \times n \times m. \end{cases}$$

The first subproblem, with the sparse matrix S fixed, is the principle component analysis (PCA) problem. The classical method to solve this is to perform singular value decomposition (SVD), sort the singular values in the descending order, and then keep the first r singular values and set the rest to zero. This gives the exact low rank matrix solution, but since SVD has cubic complexity, the algorithm is impractical for large datasets. The fast low-rank approximation method uses bilateral random projections (BRP). To approximate the low-rank matrix with rank r for a given matrix X (it would be $X-S_{t-1}$ for the first subproblem), the first step is to compute $Y_1=XA_1$ and $Y_2=X^T A_2$, where $A_1$ and $A_2$ are m×r and n×r random matrices, respectively. The rank-r approximation of X is then $Y_1(A_2^T Y_1)^{-1} Y_2^T$. The computation is fast since $A_2^T Y_1$ is a r×r matrix for a small r. The second subproblem is solved by hard-thresholding.

(3.3) Experimental Studies

In experimental studies of the present invention, the SLR method was tested on the Mitchell Science 2008 fMRI Data (see Literature Reference No. 3 for the Mitchell Science 2009 fMRI Data) in which there are m=360 fMRI brain volumes for each subject from (60 exemplars)×(6 epochs) stimuli. Each epoch ma represent a test series in which each of the exemplars was presented to one or more test subjects. Exemplars may be presented in the same or in different orders as during other epochs.

The leave-1-out (epoch) cross validation (which is described in Literature Reference No. 7) was performed for one subject. From a total of 21,764 voxels in a brain volume in the original data, n=2000 stable voxels were chosen that have the highest correlations with/across all exemplars and (6−1) epochs. Correlation for a particular voxel may be determined by considering the range of voxel values (e.g., a multidimensional vector or a high dimensional vector) for the particular voxel as measured between different exemplars and/or epochs. Correlation may be found by calculating the average pairwise correlation over all pairs (epochs) of voxel vectors (values of all exemplars for the voxel). A voxel with a high correlation means the voxel exhibits a consistent (across different epochs) variation across exemplars. Voxels are then ranked according to the calculated correlation in the descending order. Stable voxels are selected by picking the top ranked (e.g., the top 2000) voxels.

Then, the 2000×360 input brain volume matrix X was formed using the stable voxels. The SLR decomposition was then applied with GoDec software (GoDec software is described in Literature Reference No. 5). The obtained sparse part S of the decomposition is then used as the activation feature. To test this feature, pairwise exemplar classification was performed using a linear support vector machine (SVM), with a training set size=(6−1) epochs (FIG. 3, element 306). See Literature Reference No. 8 for a description of pairwise exemplar classification and a linear SVM.

Figure 5:
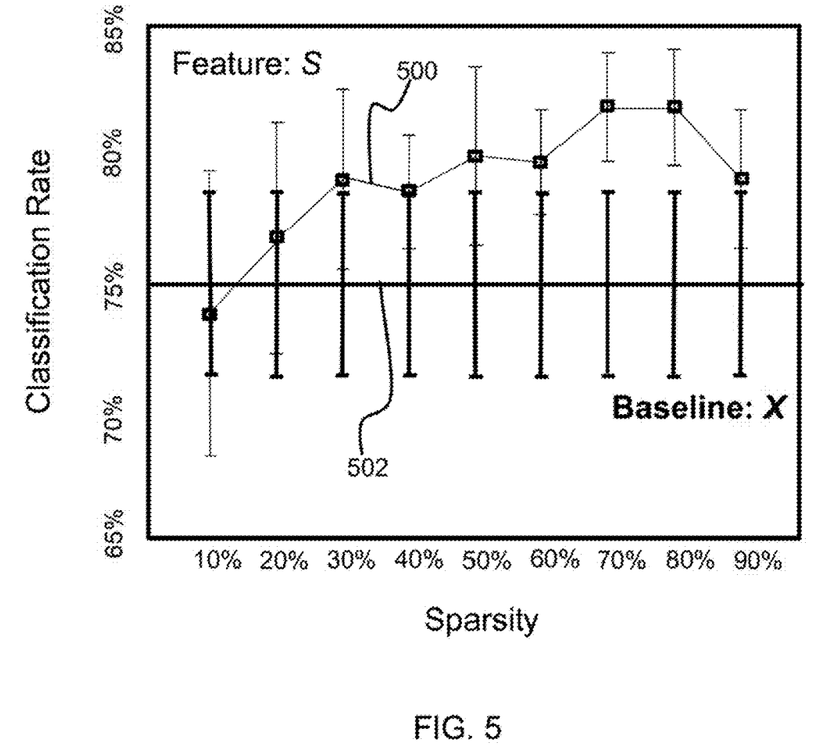
FIG. 5 is an exemplary illustration of results from the use of sparse and low-rank (SLR) decomposition for extracting neural activities in functional magnetic resonance imaging (fMRI)brain images according to the principles of the present invention.

FIG. 5 shows the classification rates using the system according to the principles of the present invention. The unbolded curve 500 represents the mean classification rates using the neural feature S (as obtained using the system according to the principles of the present invention), extracted with sparsity k ranging from 10% to 90%, with a 10% increment and rank r=3 for the low-rank matrix. The extracted neural feature for each stimuli is stored as a set of voxels (e.g, 2000 stable voxels), each having a particular vector value. The error bars show one standard deviation from the mean. As a baseline, using a conventional method, the bold line 502 represents the classification rate using the 2000 stable voxels directly. It was observed that for a large range of sparsity (along the x-axis), using the extracted feature S (i.e., the unbolded curve 500) significantly increased the classification rate (along the y-axis) for correctly using a neural signal input to identify a particular stimulus that was presented to a person. This is because the SLR decomposition is able to extract the exemplar-activated voxels from the stable voxels, while using stable voxels directly may not distinguish resting state voxels and activated voxels. The extracted neural feature is used to build the classification. The extracted neural features is used to train the classification and test the classification. For the purposes of the present invention, classification refers to identifying a neural volume as being generated by a particular stimuli.

In classifying neural signals, a linear support vector machine, L-SVM, analysis was used to assess classification performance (element 310), reflecting information content of the data. For this analysis, data was divided into training and testing sets in a cross-validation scheme, wherein one run was reserved for testing in each fold of the cross-validation, and the remaining nine runs were used for training. The classifier was trained with the voxel values from the training data and the associated stimulus labels. The learned classifier was then used to predict labels for the unlabeled testing data, which were compared to the true labels to assess percent correct performance.

In summary, the system according to the principles of the present invention is based on a unique use of sparse and low-rank (SLR) matrix decomposition to extract neural features for classification of neural activity signals. This technique will be an important component of any neural activity based classification system. The neural domains to be classified can come from any number of signals, non-limiting examples of which include fMRI blood-oxygen-level dependent (BOLD), electroencephalography (EEG), functional near-infrared spectroscopy (fNIRS), and magnetoencephalography (MEG).

The decoding of neural signals in general, whether for intent or performance monitoring, is of interest to augment human machine interfaces. Vehicle and aircraft manufacturers can use the system described herein for new neural decoding methods for vehicle operators (e.g., drivers, pilots). Neural signals (e.g., EEG signals) can be transformed and used as features in a classifier trying to detect intent: "thought" commands or responses.

Another application area for the present invention is in human subject training and learning. EEG systems have been used to infer performance in the human brain during instruction through decoding of secondary signals, such as level of attention and working memory load. The system according to the principles of the present invention can be used to discover whether the explicit knowledge during instruction is related to the structure of neural signals, such as the spatiotemporal patterns of foreground or background processing as expressed in EEG. Additionally, war tighter training and analyst training are areas of interest in government programs.

What is claimed is:

1. A system for feature transformation of neural activity, the system comprising:
   one or more processors and a non-transitory computer-readable medium having, executable instructions encoded thereon such that when executed, the one or more processors perform operations of:
   obtaining a set of neural activity signals associated with different stimuli;
   extracting a neural feature for each stimuli from the set of neural activity signals using sparse and low-rank (SLR) decomposition; and
   using the neural feature to generate a classification of the stimuli.

2. The system as set forth in claim 1, wherein the neural feature for each stimuli is stored as a set of voxels, each voxel having a vector value.

3. The system as set forth in claim 2, wherein the neural activity signals are functional magnetic resonance imaging (fMRI) neural activity signals, and wherein the one or more processors further perform operations of:
   selecting a set of stable voxel values from a collection of fMRI brain volumes associated with the different stimuli;
   from the set of stable voxel values, organizing a set of fMRI brain volumes associated with the set of stable voxel values into a matrix X;
   decomposing the matrix X into a set of matrices, including a low-rank part L matrix, a sparse part S matrix, and a Gaussian part G matrix.

4. The system as set forth in claim 3, wherein the sparse part S matrix represents a neural activation feature, the low-rank L matrix represents a neural resting state feature, and the Gaussian part G matrix represents noise.

5. The system as set forth in claim 4, wherein the neural activation feature is modeled. as a foreground in the set of neural activity signals, and the neural resting state feature is modeled as a stationary background in the set of neural activity signals.

6. The system as set forth in 5, wherein the set of stable voxel values comprises exemplar-activated voxels representing a current focus of attention, and wherein decomposing the matrix X extracts exemplar-activated voxels from the set of stable voxels.

7. The system as set forth in claim 1, wherein the neural activity signals are selected from a group consisting of functional magnetic resonance imaging (fMRI) neural activity signals, fMRI blood-oxygen-level dependent (BOLD) neural activity signals, electroencephalography (EEG) neural activity signals, functional near-infrared spectroscopy (fNIRS) neural activity signals, and magnetoencephalography (MEG) neural activity signals.

8. A computer-implemented method for feature transformation of neural activity, comprising:
   an act of causing one or more processors to execute instructions stored on a non-transitory memory such that upon execution, the one or more processors perform operations of:
   obtaining a set of neural activity signals associated with different stimuli;
   extracting a neural feature for each stimuli from the set of neural activity signals using sparse and low-rank (SLR) decomposition; and
   using the neural feature to generate a classification of the stimuli.

9. The method as set forth in Claim 8, wherein the neural feature for each stimuli is stored as a set of voxels, each voxel having a vector value.

10. The method as set forth in claim 9, wherein the neural activity signals are functional magnetic resonance imaging (fMRI) neural activity signals, and wherein the one or more processors further perform operations of:
    selecting a set of stable voxel values from a collection of fMRI brain volumes associated with the different stimuli;
    from the set of stable voxel values, organizing a set of fMRI brain volumes associated with the set of stable voxel values into a matrix X;
    decomposing the matrix X into a set of matrices, including a low-rank part L matrix, a sparse part S matrix, and a Gaussian part G matrix.

11. The method as set forth in claim 10, wherein the sparse part S matrix represents a neural activation feature, the low-rank L matrix represents a neural resting state feature, and the Gaussian part G matrix represents noise.

12. The method as set forth in claim 11, wherein the neural activation feature is modeled as a foreground in the set of neural activity signals, and the neural resting state feature is modeled as a stationary background in the set of neural activity signals.

13. The method as set forth in claim 12, wherein the set of stable voxel values comprises exemplar-activated voxels representing a current focus of attention, and wherein decomposing the matrix X extracts exemplar-activated voxels from the set of stable voxels.

14. The method as set forth in claim 8, wherein the neural activity signals are selected from a group consisting of functional magnetic resonance imaging (fMRI) neural activity signals, fMRI blood-oxygen-level dependent (BOLD) neural activity signals, electroencephalography (EEG) neural activity signals, functional near-infrared spectroscopy (fNIRS) neural activity signals, and magnetoencephalography (MEG) neural activity signals.

15. A computer program product for feature transformation of neural activity, the computer program product comprising computer-readable instructions stored on a non-transitory computer-readable medium that are executable by a computer having a processor for causing the processor to perform operations of:
    obtaining a set of neural activity signals associated with different stimuli;
    extracting a neural feature for each stimuli from the set of neural activity signals using sparse and low-rank (SLR) decomposition; and
    using the neural feature to generate a classification of the stimuli.

16. The computer program product as set forth in claim 15, wherein the neural feature for each stimuli is stored as a set of voxels, each voxel having a vector value.

17. The computer program product as set forth in claim 16, wherein the neural activity signals are functional magnetic resonance imaging (fMRI) neural activity signals, and wherein the computer program product further comprises instructions for causing the processor to perform operations of:
    selecting a set of stable voxel values from a collection of fMRI brain volumes associated with the different stimuli;
    from the set of stable voxel values, organizing a set of fMRI brain volumes associated with the set of stable voxel values into a matrix X;

decomposing the matrix X into a set of matrices, including a low-rank part L matrix, a sparse part S matrix, and a Gaussian part G matrix.

18. The computer program product as set forth in claim 17, wherein the sparse part S matrix represents a neural activation feature, the low-rank L matrix represents a neural resting state feature, and the Gaussian part G matrix represents noise.

19. The computer program product as set forth in claim 18, wherein the neural activation feature is modeled as a foreground in the set of neural activity signals, and the neural resting state feature is modeled as a stationary background in the set of neural activity signals.

20. The computer program product as set forth in claim 19, wherein the set of stable voxel values comprises exemplar-activated voxels representing a current focus of attention, and wherein decomposing the matrix X extracts exemplar-activated voxels from the set of stable voxels.

21. The computer program product as set forth in claim 15, wherein the neural activity signals are selected from a group consisting of functional magnetic resonance imaging (fMRI) neural activity signals, fMRI blood-oxygen-level dependent (BOLD) neural activity signals, electroencephalography (EEG) neural activity signals, functional near-infrared spectroscopy (fNIRS) neural activity signals, and magnetoencephalography (MEG) neural activity signals.

* * * * *